United States Patent [19]

Cincotta et al.

[11] Patent Number: 5,344,832
[45] Date of Patent: Sep. 6, 1994

[54] METHOD FOR THE LONG TERM REDUCTION OF BODY FAT STORES, INSULIN RESISTANCE, HYPERINSULINEMIA AND HYPERGLYCEMIA IN VERTEBRATES

[75] Inventors: Anthony H. Cincotta, Andover, Mass.; Albert H. Meier, Baton Rouge, La.

[73] Assignees: The Board of Supervisors of Louisiana University and Agricultural and Mechanical College, Baton Rouge, La.; Ergo Science Incorporated, Charlestown, Mass.

[21] Appl. No.: 719,745

[22] Filed: Jun. 24, 1991

Related U.S. Application Data

[63] Continuation-in-part of Ser. No. 463,327, Jan. 10, 1990, abandoned.

[51] Int. Cl.$^5$ .................... A61K 31/44; A61K 31/495
[52] U.S. Cl. .................... 514/288; 514/250; 514/866
[58] Field of Search .................... 514/250, 288, 866

[56] References Cited

U.S. PATENT DOCUMENTS

| | | | |
|---|---|---|---|
| 3,074,847 | 1/1963 | Bigsby et al. | 514/271 |
| 3,752,814 | 8/1973 | Fluckiger et al. | 544/346 |
| 3,752,888 | 8/1973 | Fluckiger et al. | 514/250 |
| 3,922,347 | 11/1975 | Bach et al. | 514/288 |
| 4,054,660 | 10/1977 | Clemens et al. | 514/288 |
| 4,239,763 | 12/1980 | Milvec et al. | 514/250 |
| 4,659,715 | 4/1987 | Meier et al. | 514/288 |
| 4,749,709 | 6/1988 | Meier et al. | 514/288 |
| 4,783,469 | 11/1988 | Meier et al. | 514/288 |

FOREIGN PATENT DOCUMENTS

| | | |
|---|---|---|
| 890369 | 3/1982 | Belgium . |
| 57-8231 | 9/1980 | Japan . |
| 2192541A | 1/1988 | United Kingdom . |

OTHER PUBLICATIONS

Wilson, *Chrono. Bio. Int.* 6:113–121, 1989.
Cincotta et al. *Life Sciences* 45:2247–2254, 1989.
Cincotta et al. *Ann Nutr Metab* 33:305–314, 1989.
Cincotta et al. *Horm Metabol Res* 21:64–68, 1989.
Cincotta et al., *J. Endocrinol.* 120:385–391, 1989.
Moore et al., *Biology of Reproduction* 36:47–58, 1987.
Cincotta et al., *Experientia* 43:416–417, 1987.

(List continued on next page.)

*Primary Examiner*—Marianne M. Cintins
*Assistant Examiner*—K. Weddington
*Attorney, Agent, or Firm*—Darby & Darby

[57] ABSTRACT

A process for the long term modification and regulation of lipid and glucose metabolism—generally to reduce obesity, insulin resistance, and hyperinsulinemia or hyperglycemia, or both (these being the hallmarks of noninsulin dependent, or Type II diabetes)—by administration to a vertebrate, animal or human, of a dopamine agonist and a prolactin stimulator. The dopamine agonist and prolactin stimulator are administered in daily dosages, respectively, at a time of day dependent on the normal circadian rhythm of fat and lean members of a similar species. Decreases in body fat deposits result by treatment of an obese species on a daily timed sequence based on circadian rhythms of the peak prolactin, or peak prolactin and peak glucocorticosteroid, blood level established for lean insulin sensitive members of a similar species. The dopamine agonist is administered at the time of, or just after the time of peak plasma prolactin concentration found in lean animals of the same species and the prolactin stimulator is administered at a time just before the plasma prolactin rhythm reaches its peak in lean animals. Insulin resistance, and hyperinsulinemia or hyperglycemia, or both, can also be controlled in humans on a long term basis by treatment corresponding to that of the treatment for obesity. The short term daily injections reset hormonal timing in the neural centers of the brain to produce long term effects.

24 Claims, No Drawings

OTHER PUBLICATIONS

Bartness et al., *J. Exp. Zoology* 244:437–454, 1987.
Emata et al., *J. Exp. Zoology* 233:29–34, 1985.
Lobato et al. *Mol and Cell. Biochem.* 67:19–23, 1985.
Cincotta et al. *J. Endocrinol.* 106:177–181, 1985.
Cincotta et al. *J. Endocrinol.* 106:173–176, 1985.
Meier et al., *Transactions of the American Fisheries Society* 113:422–431, 1984.
Eisemann et al., *J. of Animal Sci.* 59(1)95–104, 1984.
Eisemanmn et al., *J. of Animal Sci.* 59(1)86–94, 1984.
Meier et al., *Current Ornithology* 2:303–343, 1984.
Cincotta, *J. Endocrinol.* 103:141–146, 1984.
Miller et al., *J. Interdiscipl. Cycle Res.* 14(1):75–84, 1983.
Miller et al., *J. Interdiscipl. Cycle Res.* 14(2):85–94, 1982.
Ottenweller et al., *Life Sciences* 28:1033–1040, 1980.
Barnett, *Post Graduate Medical J.* 56:11–14, 1980.
Horseman et al., *General and Comparative Endocrinology* 38:269–274, 1979.
Horseman et al., *J. Endocr.* 82:367–372, 1979.
Meier et al., Circadian hormone basis for seasonal conditions in the gulf killifish *Fundulus grandis*. In Comparative Endocrinology, 141–144. Galliard et al. (eds), Elsevier/North Holland Biomedical Press, Amsterdam (1978).
Spieler et al., *Life Sciences* 22:255–258, 1977.
Meier et al., *amer. J. of Physiology* 232(2):E193–E196, 1977.
Meier et al., *Amer. Zool.* 16:649–659, 1976.
Meier et al., *General and Comparative Endocrinology* 26:253–258, 1975.
Meier, *Amer. Scientist* 61(2)184–187, 1973.
Berle, *Acta endocr. Suppl.* 173, Abstract No. 104, 1973.
Meier et al., *Biology of Reproduction* 8:400–410, 1973.
Meier et al., *General and Comparative Endocrinology* Suppl. 3:499–508, 1972.
Meier et al., *Proc. Soc. for Exp. Bio. & Med.* 137:408–415, 1971.
Meier et al., *Gen. & Comp. Endocrin.* 17:311–318, 1971.
Joseph et al., *J. Exp. Zool.* 178(1):59–62, 1971.
Meier et al., *Science* 173:1240–42, 1971.
Meier et al., *Proc. Soc. Exp. Biol. and Med.* 133(4):1113–16, 1970.
Lee et al., *J. of Exp. Zool.* 166(3):307–316, 1967.
Meier et al., *Gen. & Comp. Endocrin.* 8(1):110–114, 1967.
Chemical Abstracts (109:66888w) 1988.
(1989) *Acta. Diabetol. Lat.*, vol. No. 26(2), pp. 133–145.
(1982) *Chemical Abstracts*, vol. No. 96, No. 11, Abstract No. 80405f.
(1990) *Chemical Abstracts*, vol. No. 112, No. 21, Abstract No. 191532p.
(1984) *Chemical Abstracts*, vol. No. 101, No. 7, Abstract No. 49205p.
(1982) *Chemical Abstracts*, vol. No. 97, No. 19, Abstract No. 156398a.
(1982) *Chemical Abstracts*, vol. No. 97, No. 3, Abstract No. 17600w.
(1981) *Chemical Abstracts*, vol. No. 95, No. 1, Abstract No. 530j.
(1980) *chemical Abstracts*, vol. No. 93, No. 13, Abstract No. 125921c.
(1979) *Chemical Abstracts*, vol. No. 91, No. 5, Abstract No. 36590k.

METHOD FOR THE LONG TERM REDUCTION OF BODY FAT STORES, INSULIN RESISTANCE, HYPERINSULINEMIA AND HYPERGLYCEMIA IN VERTEBRATES

RELATED APPLICATIONS

This invention is a continuation-in-part of copending U.S. application Ser. No. 463,327, filed Jan. 10, 1990 by Anthony H. Cincotta and Albert H. Meier.

FIELD OF THE INVENTION

This invention relates to an improved process for the reduction in vertebrates, animals or humans, of body fat stores, and reduction of insulin resistance, hyperinsulinemia, which is often associated with insulin resistance, and hyperglycemia, or reduction of plasma glucose. In particular, it relates to a process requiring the timed daily administrations of a dopamine agonist and a prolactin stimulator at appropriate preselected times of day, and preferably also a thyroid hormone, to reduce and control over an extended period the stated pathologies which, with obesity, arc pathologies characteristic of the onset of noninsulin dependent, or Type II diabetes.

BACKGROUND

In U.S. Pat. No. 4,659,715, which issued Apr. 21, 1987 to Albert H. Meier and Anthony H. Cincotta, there is disclosed a method for the reduction in vertebrate animals of body fat stores, without concomitant decrease in muscle mass, via the administration of multiple daily doses over prescribed periods of a prolactin-inhibiting, or dopamine compound. This method, which is associated with an altered livid metabolism, offers hope to those suffering with obesity; a serious worldwide health problem.

In pending U.S. application Ser. No. 463,327, supra, there is disclosed a method, or process, for the long term modification and regulation of livid metabolism in a vertebrate, animal or human, not only to reduce obesity, but also to reduce insulin resistance, and hyperinsulinemia or hyperglycemia, or both, by administration to a subject of a prolactin-inhibiting compound, or dopamine agonist. The role of prolactin in a vertebrate species to control these pathologies (the hallmarks of noninsulin dependent, or Type II diabetes), it was found, was crucial! The level of prolactin in the blood of a species is time-of-day dependent, and cyclic, its level in the blood rising and falling at different times of day dependent on the amount of fat deposited in the body of the subject. The phase relationships between the rise and fall of prolactin which appears in the blood streams of obese and lean subjects, respectively, are different. Administration of the dopamine agonist, it is disclosed, is made over a limited period at a time of day dependent on the normal circadian rhythm of fat and lean members, respectively, of a similar species based on the result to be achieved. Where, e.g., it is desired to reduce the body fat of a subject, decreases in body fat deposits are produced by treatment of the obese species on a timed daily sequence based on circadian rhythms of the peak prolactin, or peak prolactin and peak glucocorticosteroid, blood level established for lean members of a similar species. A person, whether lean or obese, showing the effects of insulin resistance, or hyperinsulinemia and/or hyperglycemia, or both insulin resistance and hyperinsulinemia and/or hyperglycemia, treated with the dopamine agonist or prolactin-inhibiting compound, in the same manner as a person suffering with obesity, it was found would become more sensitive to insulin, and the effects of hyperinsulinemia and/or hyperglycemia would be reduced on a long term basis. Thus, insulin resistance, and hyperinsulinemia or hyperglycemia, or both, like obesity, can be controlled in humans on a long term basis by treatments corresponding to that for the treatment of obesity to lower fat deposits in the body of the subject.

Albeit the administration to obese subjects of a prolactin-inhibiting compound on a time-of-day schedule related to a daily prolactin secretion cycle mimicking that of a lean subject to cause the obese subject to lose body fat, the results have proven less than 100 percent effective. For example, in treating a large population of obese subjects to reduce body fat during the winter months, a significant reduction in body fat occurred in the majority of the treated patients. On the other hand, it was observed that a lower percentage of a population of obese patients similarly treated during the summer months showed a significant reduction in body fat. This suggests that prolactin secretions in a subject are to some extent seasonal, but equally if not more important it suggests that better timing and control of prolactin secretions in a subject, particularly during the summer months, can improve and render more effective the liporegulatory nature of the treatments to reduce obesity, reduce insulin resistance, and hyperinsulinemia or hyperglycemia, or both.

OBJECTS

It is, accordingly, a primary objective of this invention to provide further improvements in a method for the long term modification and regulation of lipid metabolism to alter, phase shift and reset on a long term, or permanent basis, circadian hormonal timing mechanisms in the neural centers of the brain.

In particular, it is an object to provide a process for resetting the circadian neural center of vertebrate animals, including humans, to alter neural centers which stimulate and control prolactin secretion to produce long lasting changes in the amount of body fat stores, the sensitivity of the cellular response of a species to insulin, and overcome hyperinsulinemia and/or hyperglycemia, which generally accompanies insulin resistance.

A more specific object is to provide a process for resetting the circadian neural centers of animals, including humans, which regulate and control lipogenesis to decrease obesity and maintain the more normal body fat stores of a lean animal, or lean human, on a long term basis.

A further, and equally specific object is to provide a process for resetting on a long term basis the circadian neural centers, particularly in humans, which regulate and control the sensitivity and responsiveness of the cells to insulin, and suppress hyperinsulinemia or hyperglycemia, or both.

THE INVENTION

These objects and others are achieved in accordance with this invention, a process which embodies in addition to the administration of a dopamine agonist, e.g. L-DOPA or bromocriptine, on a timed daily basis to modify and reset the neural circadian oscillation expressed by the prolactin rhythm (prolactin oscillation)

of a vertebrate animal or human subject, or both the prolactin and glucocorticosteroid (glucocorticosteroid oscillation) rhythms of said subject, administering on a timed daily basis at a different predetermined time of day a prolactin stimulator, e.g. metoclopramide (Reglan), in dosage amount sufficient to increase hormonal prolactin secretion in the blood of the subject to better control and regulate the prolactin rhythm, or both the prolactin and glucocorticosteroid rhythms, of the subject. Administration of the dopamine agonist, continued on a daily basis over a sufficient period of time, as disclosed in U.S. application Ser. No. 463,327, supra, can be employed to increase the hyperglycemic sensitivity to insulin, reduce body fat stores, suppress hyperinsulinemia and reduce hyperglycemia in a subject, to reset long term on cessation of the daily dosages of the dopamine agonist the neural phase oscillation of the prolactin rhythm, or both the prolactin and glucocorticosteroid rhythms, in a subject; and the administration of the dopamine agonist and additionally the prolactin stimulator at a different predetermined time of day can be employed to control, regulate, and reset on a long term basis these circadian neural hormonal expression, and correct these pathologies, with higher consistency and greater effectiveness than by, administration of the dopamine agonist alone. In treating a large subject population of obese persons, during the summer months when the success rate is lower than the winter months, with a dopamine agonist alone to regulate lipid metabolism and reduce fat deposits in the bodies of these subjects, success was achieved in about 60 percent of the patients treated. In contrast, in treating a second large subject population of obese persons over a similar period of time during the summer months with a similar dopamine agonist and additionally, a prolactin stimulator, success was achieved in about 85 percent of the population, an improvement of about 25 percent. The weight loss of body fat in a group treated with both the dopamine agonist and the prolactin stimulator, measured on a weekly basis during the period of treatment, is almost double that of the group treated with the dopamine agonist alone.

The efficacy of treatment with the dopamine agonist and prolactin stimulator can also be improved by daily thyroid hormone administration to a subject; particularly hypothyroid subjects. Exemplary thyroid hormones are, e.g., thyroxine, triiodothyronine, synthroid and other thyroxine analogs. The thyroid hormones are given daily, once a day, suitably in the morning after waking. Suitably, the thyroid hormone is given at dosage levels ranging from about 0.1 to about 0.4 milligrams per day, preferably from about 0.2 to about 0.35 milligrams per day.

In the practice of this invention, the dopamine agonist, or prolactin-inhibiting compound, and prolactin stimulator are administered daily to a subject orally or by subcutaneous, intravenous or intramuscular injections, at different times of day, to alter the prolactin rhythm from that of a lean subject to that of an obese subject of the same species, or as is most often the objective to alter the prolactin rhythm from that of an obese subject to that of a lean subject of the same species. In treating a subject to alter, reset, and phase shift the prolactin rhythm from that of an obese subject to that of a lean subject, administration of the dopamine agonist and prolactin stimulator can not only be employed to reduce body fat stores, or obesity, in an obese subject, but also to reduce insulin resistance, hyperinsulinemia or hyperglycemia, or both hyperinsulinemia and hyperglycemia, in a subject, obese or lean, exhibiting any one, or all of these symptoms desirable of change. In carrying out this process, where it is desired to modify, phase shift, and reset the prolactin rhythm of a subject to that of a lean animal, to reduce body fat stores if the subject is obese, increase sensitivity response to insulin whether the subject is lean or obese, and suppress hyperinsulinemia or hyperglycemia, or both, whether the subject is lean or obese, the dopamine agonist is administered in daily dosage amount sufficient to decrease, or reduce hormonal prolactin secretion in the blood of the subject at a time or just after the time of day corresponding to that when the prolactin level in the blood of a lean insulin sensitive subject is at a peak, and the prolactin stimulator is administered in dosage amount sufficient to increase hormonal prolactin secretion in the blood of the subject at a time or near the time of day when the prolactin level in the blood of a lean insulin sensitive subject is at its lowest point, or point of maximum depression; this occurring just before the prolactin level rises to a peak in a lean insulin sensitive subject. Thus, a prolactin-inhibiting compound, preferably an ergot-related prolactin-inhibiting compound, is administered to a subject exhibiting any one or more of the symptoms desirable of change, e.g., obesity, insulin resistance, hyperinsulinemia or hyperglycemia at a time of day when plasma prolactin levels are low in lean insulin sensitive subjects of the same species. Exemplary of prolactin-inhibiting, ergot-related compounds are: 2-bromo-alpha-ergocryptine; 6-methyl-8 beta-carbobenzyloxy-aminoethyl-10 alpha-ergoline; 8-acylaminoergolenes, such as 6-methyl-8 alpha-(N-acyl)amino-9-ergoline and 6-methyl-8 alpha-(N-phenylacetyl)amino-9-ergoline; ergocornine; 9,10-dihydroergocornine; and D-2-halo-6-alkyl-8-substituted ergolines, e.g., D-2-bromo-6-methyl-8-cyanomethylergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention. A prolactin stimulator is administered to the same subject just before that time of day when daily plasma prolactin levels are highest in lean insulin sensitive subjects of the same species (i.e., before the onset of sleep). Exemplary of prolactin stimulators are dopamine antagonists, i.e. metoclopramide, haloperidol, pimozide, phenothiazine, sulpiride, chlorpromazine and serotonin agonists, i.e. MAO inhibitors, e.g. pargyline, synthetic morphine analogs, e.g. methadone, antiemetics, e.g. metoclopramide, antipsychotics, e.g. sulpiride, estrogens and others, e.g. tryptophan and 5-hydroxy-tryptophan.

In the treatment of an animal, or human subject, the stores of body fat can be depleted or increased, the treatments continued until the stores of body fat are stabilized at an optimum or near optimum level dependent on the level of body fat stores desired in the subject, for time sufficient that on termination of the treatment the prolactin rhythm, and preferably both the prolactin and glucocorticosteroid rhythms, are reset to maintain on a long term basis the reduced, or increased, body weight stores. In humans, the objective is almost invariably to reduce body fat stores, and obesity. It has been established that a relationship exists between obesity and insulin resistance, and that obesity can lead to increased insulin resistance. Likewise, it has been established that the circadian rhythms of plasma prolactin and glucocorticosteroid concentrations, respectively, differ in lean and fat animals as well as in insulin sensitive animals and animals that are insulin resistant (decreased insulin stimulated glucose disposal). In a fat animal, prolactin will reach a peak level at a given hour of a 24 hour period (in a human, usually near midday), and the prolactin level of a lean animal at another time of day (in a human usually during sleep). In a lean animal the glucocorticosteroids, e.g., cortisol, will peak during a 24 hour period at a given hour (generally at a time different from that of prolactin); in a human generally several hours after waking. Thus, the phase relations of the cortisol and prolactin rhythms differ in lean and fat animals. The peak periods of prolactin and glucocorticosteroid production, respectively, may differ to some extent between males and females of any given species. In carrying out the invention process, a daily dosage of a dopamine agonist, or prolactin inhibitor, is given to an obese subject shortly after the normal time of day that the prolactin is at its peak in a lean insulin sensitive subject of the same species and sex, and daily dosages of a prolactin stimulator are given to the same obese subject (in conjunction with the prolactin inhibitor) shortly before the normal time of day that the prolactin is at its peak in a lean insulin sensitive subject of the same species and sex, to produce a body fat weight reduction in the obese subject. Such treatments will if continued over a sufficient period, reset on a long term or permanent basis the phase of the neural oscillation for the prolactin rhythm, or the phases of the neural oscillations for both the prolactin and glucocorticosteroid rhythms in the obese insulin resistant subject to that present in a lean insulin sensitive subject. The obese subject, on initiation of the treatment with the dopamine agonist, or prolactin inhibitor in conjunction with the prolactin stimulator, will lose body fat stores, and the body fat deposits of the obese subject on continuation of the treatments on a daily basis will drop to and stabilize at that of a lean subject of the same species. On discontinuing the daily treatments, the rise and fall of the prolactin, or prolactin and glucocorticosteroid levels in the blood of the treated patient on a daily basis will correspond to that of a lean insulin sensitive subject of the same species, and for a period of long duration. The effect of resetting the prolactin, or prolactin and glucocorticosteroid rhythms, in this manner in a subject exhibiting any one or more of the symptoms desirable of change, i.e., insulin resistance, hyperinsulinemia or hyperglycemia, whether the subject is lean or obese (and loses body fat stores) also increases the sensitivity of the cells of the subject to insulin, reduces hyperinsulinemia or hyperglycemia, or both, and thus alters long term pathologies which are characteristics of the onset of Type II diabetes.

In treating vertebrates, generally, dosages of the dopamine agonist, and prolactin stimulator, respectively, are each given, generally once a day, on a daily basis, generally over a period ranging from about 10 days to about 150 days. The dopamine agonist is given daily at dosage levels ranging from about 3 micrograms to about 100 micrograms, preferably from about 8 micrograms to about 20 micrograms, per pound of body weight, and the prolactin stimulator is given daily at dosage levels ranging from about 10 micrograms to about 100 micrograms, preferably from about 20 micrograms to about 50 micrograms, per pound of body weight to modify, or alter, and continued for a time sufficient to reset the circadian plasma prolactin rhythm.

In treating humans, the dopamine agonist, or prolactin inhibitor, is generally given at daily dosage levels ranging from about 3 micrograms to about 20 micrograms, preferably from about 4 micrograms to about 12 micrograms, per pound of body weight, and the prolactin stimulator is generally given at daily dosage levels ranging from about 10 micrograms to about 100 micrograms, preferably from about 20 micrograms to about 50 micrograms, per pound of body weight. Such treatments continued over a period of time ranging from about 30 days to about 60 days will modify and reset the lipid and glucose metabolism of the obese person to that of a lean person, if given to an obese person daily so that the prolactin inhibitor is given just a short period after the typical daily peak of plasma prolactin concentration in a lean person and the prolactin stimulator is given a short period before plasma prolactin peaks in a lean person. Body fat deposits, inclusive of adipose, arterial wall and plasma fat, within the obese person will be reduced, leveled out and maintained after the treatments are discontinued at that of a lean person, over an extended period of time. A person showing the effects of insulin resistance, or hyperinsulinemia and/or hyperglycemia, or both insulin resistance and hyperinsulinemia and/or hyperglycemia, treated with the dopamine agonist, or prolactin inhibitor, and a prolactin stimulator at similarly appropriate times of day, will become more sensitive to insulin (i.e., will have a lower insulin resistance), and the effects of hyperinsulinemia and/or hyperglycemia will be reduced on a long term basis. The injections of the dopamine agonist, or prolactin inhibitor, and prolactin stimulator, in this manner will thus reset the phase relations of the two neural oscillations and their multiple circadian expressions to alter metabolism on a long term basis, if not permanently. In other words, there will be as a result of the timed daily dosages of the dopamine agonist, or prolactin inhibitor, and prolactin stimulator, a long term reversal of the major pathologies generally associated with the development of Type II diabetes. The levels of body fat stores, plasma insulin concentrations, insulin resistance, and hyperglycemia, or all of these pathologies can be reduced on a long term basis by such treatment, or treatments, from the high levels often found in obese, hyperinsulinemic persons to that of the much lower and much more desirable levels found in lean euinsulinemic persons.

The dopamine agonist is administered to a subject, particularly a human, exhibiting symptoms to be controlled at a time, or just after the time the prolactin concentration reaches its peak in the plasma of a lean subject, particularly a lean insulin sensitive subject, generally within about 2 hours to about 8 hours, preferably within about 4 hours to about 6 hours after the peak would occur in a lean subject, particularly a lean insulin sensitive subject. The prolactin stimulator is administered at a time just before the plasma prolactin rhythm found in a lean subject reaches its peak, generally from about 2 hours to about 4 hours, preferably from about 2 hours to about 3 hours, before the plasma protein has reached it peak in a lean person. Administration of the prolactin stimulator just before sleep has been found highly satisfactory.

The responsiveness of the timed daily treatments with the dopamine agonist and prolactin stimulator can be further improved by the administration of daily dosages of thyroid hormones, particularly in the treatment of hypothyroid subjects or subjects whose blood during certain times of the year appear deficient in thyroid hormones. It is known, e.g., that the circadian rhythm of response to prolactin depends on adequate thyroid hormone (John, Meier and Bryant, *Physiological Zoology* 45, pp. 34–42, 1972); and that the circadian rhythms of cortisol and prolactin responses are also dependent on thyroid hormone (Meier, *Endocrinology* 98, pp. 1474–1479, 1976: Ottenweller and Hedge, *Life Sciences* 28, pp. 1023–1040, 1981). Studies have shown that the further administration of thyroid hormones on a daily basis with the dopamine agonist and prolactin stimulator increase the responsiveness of many hypothyroid, near hypothyroid, and seasonally hypothyroid subject types to such treatments. It is accordingly a further preferred feature of this invention to administer once a day on a daily basis, besides the dopamine agonist and prolactin stimulator, thyroid hormone at dosage levels ranging from about 0.1 milligrams to about 0.4 milligrams, preferably from about 0.2 milligrams to about 0.35 milligrams the levels of body fat, plasma triglyceride, plasma cholesterol and the symptoms, or pathologies associated with Type II diabetes can be lowered on a long term basis by such treatment; and the treatment rendered more effective in hypothyroid individuals.

In terms of the human subject, "obesity can be defined as that body weight over twenty percent above the ideal body weight for a given population" (R. H. Williams, *Textbook of Endocrinology*, 1974, pp. 904–916). The time of day when the prolactin and glucocorticosteroid levels, respectively, will peak in the blood of humans during the day differs between obese subjects and lean subjects, and the peak in each type of subject can be readily determined by measurement of the fat and lean specimens, as defined. In other animal species what constitutes obese and lean members, respectively, of a species can be readily determined by body weight patterns correlated with the prolactin and glucocorticosteroid levels, respectively, in the plasma of lean and obese members, respectively. The levels differ between members of the different species, but among members of the same species there is close correlation between prolactin and glucocorticosterone levels, respectively, at certain times of the day dependent on the obesity or leanness of a given specimen.

These and other features of the invention will be better understood by reference to the following information and data of experimental work with animals and humans. In the examples the terminology "LD" refers to the light/dark cycle, the first number following the expression LD refers to the hours of light, and the second to the hours of darkness in the cycle. Thus LD 14:10 refers to a cycle having 14 hours of light and 10 hours of darkness, and this period of the day is expressed in terms of 2400 hours. The letter n refers to the number of animals in a group, "BW" designates body weight, g represents grams, mg represents milligrams, and "ub" is an expression of micrograms.

In the following examples, data are given which show the altered phase relationships of the circadian rhythms of plasma corticosteroid and prolactin concentrations; changes beneficial in the treatment of diabetics.

EXAMPLE 1

A 44 year old obese woman weighing 198 pounds was given bromocriptine tablets (2.5 mg/day), taken orally, shortly after waking in the morning, and metoclopramide tablets (10 mg/day), taken orally, just before sleep late at night. After 6 weeks of treatment, body weight was reduced by 5 pounds without dieting or increased exercise. The percentage body fat determined by skinfold measurements was reduced from 35.4 to 32.3. This reduction is equivalent to a loss of 7.7 pounds of body fat, from 70.0 pounds to 62.3 pounds. Loss of fat exceeding loss of body weight is a general characteristic of this treatment that sharply differentiates it from diet programs in which considerable protein, carbohydrate and water is lost in addition to fat.

EXAMPLE 2

A hypothyroid 58 year old woman who was mildly obese responded poorly to bromocriptine (1.25 mg) taken orally daily 2 hours after waking for 3 months. A change in treatment to a combination of bromocriptine and metoclopramide (Reglan), a prolactin stimulator, in conjunction with an increase of thyroid hormone (Synthroid) from 0.2 to 0.35 mg daily, produced dramatic losses in both body fat stores and body weight. Oral dosages of bromocriptine (1.25 mg) were taken daily 2 hours after waking and metoclopramide (5 mg) was taken orally immediately before sleep. Synthroid was taken orally (0.35 mg/day) within 2 hours after waking. After 6 weeks, body weight was reduced from 161 to 145 pounds without a restriction on food consumption or increased exercise regimen. Body fat stores determined by skinfold measurements were reduced by 8.5 pounds, from a total fat content of 53.8 pounds to 45.3 pounds. The subject claimed she had not been so lean nor weighed so little in 22 years. Further decreases in body fat and body weight were evident after 20 weeks of treatment. Weight was reduced from 161 lbs (initial) to 125 lbs and fat was reduced by a total of 20.6 lbs. In addition, plasma concentrations of total cholesterol and triglyceride were reduced by such treatment after 20 weeks, the initial and final cholesterol levels were 237 and 152 mg/dl, respectively. The initial and final triglyceride levels were 1191 and 161 mg./dl, respectively. This combination of prolactin inhibitor (bromocriptine), prolactin stimulator (metoclopramide) and thyroid hormone has been found especially useful for resetting circadian rhythms in hypothyroid individuals who have rhythms of low amplitude that are resistant to resetting by bromocriptine alone.

EXAMPLE 3

A 57 year old obese woman was given orally 1.25 mg bromocriptine daily one hour after waking and 10 mg metoclopramide shortly before sleep. After 2 weeks, body weight was reduced from 194 to 189 pounds and percentage body fat, determined from skinfold measurements, was reduced from 39.5 to 38.1. The fat loss, then, in 2 weeks was 4.6 pounds, accounting for almost all of the body weight loss.

EXAMPLE 4

A 63 years old obese woman was given orally 1.24 mg bromocriptine daily at one hour after waking and 2.5 mg bromocriptine 6 hours after waking. Metoclopramide (10 mg) was given orally immediately before sleep. After 19 days, percentage body fat, determined by skinfold measurements, was reduced from 37.1 to 35.5. This is a loss of 2.1 pounds of fat without food restriction, increased exercise or loss of body weight.

EXAMPLE 5

A 60 year old obese woman with Type II diabetes was given orally 1.25 mg bromocriptine daily at one hour after waking and 10 mg metoclopramide immediately before sleep. After 6 weeks, body fat was reduced from 108.3 lbs (initial) to 97.9 lbs. Fasting blood glucose levels were reduced from 126 mg/dl (initial) to normal levels (near 100 mg/dl). Furthermore, the daily dose of the hypoglycemic drug she took for treatment of diabetes (micronase) was reduced from 5.0 to 2.5 mg midway during the bromocriptine/metoclopramide treatment.

EXAMPLE 6

An obese 55 year old man weighing 285 pounds with Type II diabetes was given orally 2.5 mg bromocriptine daily one hour after waking and 10 mg metoclopramide immediately before sleep. He lost 11 pounds of fat during 8 weeks of treatment. Fasting blood glucose levels were 180 mg/dl prior to treatment. After 4 weeks of treatment, blood glucose levels were near normal (100 mg/dl) and diabetic treatment with a hypoglycemic drug (micronase) was discontinued. After 8 weeks of bromocriptine and metoclopramide treatment, the fasting glucose was 104 mg/dl.

EXAMPLE 7

Three post menopausal women (Subjects A, B and C) with high initial levels of body fat (40.6, A; 37.1, B; and 39.5, C; % body weight), as indicated by skinfold measurements, were treated orally with 1.25 mg bromocriptine taken within one hour of waking and 5 mg metoclopramide taken immediately before sleep. Body fat was reduced by 5.8 lbs after 7 weeks (Subject A), 5.1 lbs after 5 weeks (Subject B) and 6.5 lbs after 4 weeks (Subject C).

EXAMPLE 8

Two control groups of adult human subjects, a first control group of seven patients was treated daily through the warm months with bromocriptine alone, and a second control group of ten patients was treated during the same period daily with both bromocriptine and metoclopramide. In the first control group the bromocriptine was administered once a day orally in dosage levels of 1.25 mg and 2.5 mg, respectively, in the morning just after waking. The second group was similarly treated, except that each person in this group was additionally given daily by mouth at bedtime 10 mg of the metoclopramide. The treatments were continued daily over periods ranging up to 16 weeks. During the period of treatment the body fat content of each patient was determined from skinfold measurements (suprailiac, subscapular, triceps and biceps). The number of weeks of treatment, the total decrease in body fat (lbs.) during the period, and the average body fat loss (lbs.) per week for each individual of the two groups are given in the Table.

TABLE

Reductions of Body Fat in Adult Human Subjects[1] Treated with Bromocriptine Alone, and Both Bromocriptine and Metoclopramide, Respectively

| Treatment | Initials of Subjects | Weeks of Treatment | Decrease in Body Fat (lbs) | Fat Loss Per Week (lbs) |
|---|---|---|---|---|
| Bromocriptine | PC | 9 | 3.5 | 0.39 |
| | JL | 12 | 5.3 | 0.44 |
| | FB | 6 | 8.8 | 1.47 |
| | JA | 6 | 1.7 | 0.28 |
| | JW-1 | 8 | 5.1 | 0.64 |
| | JW-2 | 8 | 1.9 | 0.24 |
| | BH | 6 | 2.0 | 0.33 |
| | Mean ± SEM | 7.8 ± 2.2 | 4.0 ± 2.6 | 0.54 ± 0.17 |
| Bromocriptine + Metoclopramide | MM | 6 | 4.6 | 0.77 |
| | AM-1 | 16 | 16.5 | 1.03 |
| | TC | 3 | 6.4 | 2.13 |
| | MH | 6 | 3.1 | 0.52 |
| | BR | 3 | 3.7 | 1.23 |
| | WH | 6 | 3.1 | 0.52 |
| | AM-2 | 5 | 5.1 | 1.02 |
| | LG | 4 | 6.5 | 1.62 |
| | HG | 5 | 3.7 | 0.74 |
| | JW | 8 | 5.8 | 0.72 |
| | Mean ± SEM | 6.2 ± 3.1 | 5.9 ± 3.3 | 0.95 ± 0.16[2] |

[1]Mean body weight was 175 lbs and mean % body fat, initially, was 33.5 (58.6 lbs fat).
[2]This value differs ($p < 0.05$; Student's t) from that of subjects treated with bromocriptine, alone.

These data show that the average body fat loss per week for the group treated with both bromocriptine and metoclopramide was essentially double that of the group treated with bromocriptine along. Moreover, the total decrease in body fat over the period was higher for the group treated with both bromocriptine and metoclopramide. It was found that the treatment of a subject with both bromocriptine and metoclopramide vis-a-vis treatment of a subject with bromocriptine alone is more effective during the summer months than during the winter months.

The data show that metabolic states are regulated at least in part by an interaction of circadian neuroendocrine rhythms. It is believed that the daily rhythms of cortisol and prolactin are individual expression of two separate circadian systems and that the daily injections of these hormones can reset the phase relations of these two systems. Thus, in a hamster model it has been found that the 0-hour relation resets the circadian oscillations into a pattern that maintains the lean, insulin sensitive state and the 12-hour relation permits retention of a pattern that maintains the obese, insulin resistant state. The effects of timed injections of a dopamine agonist, or prolactin-inhibiting compound, it has been found are long lasting. Apparently once reset, the phase relation of the two circadian oscillations tends to maintain its altered pattern.

Changes in the phase relations of two circadian neuroendocrine oscillations are evidenced by changes in the phase relations of their circadian expression. This expectation is fulfilled respecting plasma glucocorticosteroid and prolactin rhythms. In several species examined, the phase relations of the two hormone rhythms differ in lean and fat animals.

The phase relation between the circadian rhythm of plasma insulin concentration and the rhythm of lipogenic responsiveness to insulin is shown to differ in lean and fat animals. Whereas the daily interval of lipogenic responsiveness remains near light onset, the phase of the insulin rhythm varies markedly. The peak concentration of insulin, e.g. occurs near light onset in obese female hamsters held on short day lengths. That is, the daily peaks of the lipogenic stimulus (i.e., insulin) and the lipogenic response to insulin coincide in fat animals and not in lean animals.

The phase relations of both prolactin and insulin rhythms as well as the rhythms of tissue responses to the hormones are important elements in the regulation of lipogenesis. Phase malfunctions in these and perhaps other rhythms may also account for insulin resistance.

It is apparent that various modification and changes can be made without departing the spirit and scope of this invention.

Having described the invention, what is claimed is:

1. A method for modifying and regulating at least one of the lipid and glucose metabolism in a vertebrate animal or human subject in need of such treatment comprising:

administering a dopamine agonist to said subject on a times daily basis at a first predetermined time of day in a first dosage amount sufficient to reduce the hormonal prolactin level in the blood of said subject; and additionally administering a prolactin stimulator to said subject on a time daily basis at a second predetermined time of day in a second dosage amount sufficient to increase hormonal prolactin level in the blood of said subject;

continuing said administrations for periods of time sufficient to modify and reset on a long-term basis the subject's daily prolactin cycle to cause it to mimic the low level and peak of the daily prolactin cycle of a lean healthy member of the same species, thereby achieving in said subject at least one of the following modifications in lipid and glucose metabolism: decrease in insulin resistance, reduction in fat stores, suppression of hyperinsulinemia and reduction of hyperglycemia.

2. The method of claim 1 wherein said subject is a human and wherein said administration are continued for periods of time sufficient to modify and reset on a long-term basis the subject's daily prolactin cycle to cause it to mimic the low day level and the nightly time peak of the daily prolactin cycle of a lean healthy human.

3. The method of claim 1 further comprising discontinuing said administrations after lapse of said periods of time, said modifications persisting over the long-term after cessation of said administrations.

4. The method of claim 1 wherein the dopamine agonist and prolactin stimulator are administered respectively on timed daily bases to said subject in amounts and for periods of time sufficient to modify and reset on a long-term basis the daily cycles of both prolactin and glucocorticosteroid in said subject.

5. The method of claim 1 wherein the timed daily dosages of the dopamine agonist and prolactin stimulator are given daily, once a day, over a period ranging from about 10 days to about 150 days, the dopamine agonist being administered in an amount within the range from about 3 micrograms to about 100 micrograms, per pound of body weight, and the prolactin stimulator being administered in an amount within the range from about 10 micrograms to about 100 micrograms per pound of body weight.

6. The method of claim 1 wherein said subject is a human and the timed dosages of the dopamine agonist are given daily, once a day, in an amount within the range from about 3 micrograms to about 20 micrograms, per pound of body weight, and the timed dosages of the prolactin stimulator are given daily, once a day, in an amount ranging from about 10 micrograms to about 100 micrograms, per pound of body weight.

7. The method of claim 6 wherein the subject is an obese human and the dopamine agonist is given daily at a time ranging from about 2 hours to about 8 hours after the time at which the prolactin concentration peaks in a lean human to modify and reset the lipid metabolism of the obese human to that of a lean human.

8. The method of claim 1 wherein the dopamine agonist is selected from the group consisting of 6-methyl-8-beta-carbobenzyloxy-aminoethyl-10 alpha-ergoline; 1,6-dimethyl-8-beta-carbobenzyloxy-aminoethyl-10 alpha-ergoline; 8-acylaminoergolenes; ergocornine; 9,10-dihydroergocornine; bromocriptine, and D-2-halo-6-alkyl-8-substituted ergolines.

9. The method of claim 1 wherein the prolactin stimulator is selected from the group consisting of metoclopramide, haloperidol, pimozide, phenothiazine, sulpiride, chlorpromazine and serotonin agonists.

10. The method of claim 1 comprising further administering to said subject thyroid hormone, daily, in an amount within the range from about 0.1 milligrams to about 0.4 milligrams.

11. A method for modifying and resetting the neutral phase oscillations of the brain which control prolactin levels in the bloodstream of a vertebrate animal or human subject, the method comprising administering a dopamine agonist and a prolactin stimulator to said subject on a daily basis at different times predetermined to produce a change of the plasma prolactin rhythm of said subject to mimic that of a lean insulin-sensitive subject, said administrations continuing for periods of time sufficient to increase the cellular sensitivity of the subject to insulin and reduce hyperglycemia, said increase and reduction persisting after cessation of said administrations.

12. The method of claim 11 wherein the dopamine agonist and prolactin stimulator are administered to the subject to also reduce hyperinsulinemia.

13. A method for modifying and resetting the neutral phase oscillations of both the prolactin and glucocorticosteroid rhythms in an obese insulin resistant vertebrate animal or human subject, which comprises administering a dopamine agonist to said obese insulin-resistant subject on a daily basis at a time of day just after the time that the prolactin level will reach its daily peak in the blood of a lean insulin-sensitive subject, in a dosage amount ranging from about 3 micrograms to about 20 micrograms, per pound of body weight, and additionally administering a prolactin stimulator to said obese insulin-resistant subject on a daily basis at a time of day just before the prolactin level will peak in the blood of a lean insulin-sensitive member of the same species, in a dosage amount ranging from abut 10 micrograms to about 100 micrograms, per pound of body weight, and continuing the administrations over periods of time ranging from 10 days to 150 days sufficient to at least begin reducing the fat deposits in the body of the obese insulin-resistant subject to that of the lean insulin-sensitive member, such that on cessation of said administrations the fat deposits in the body of the treated subject will continue to be reduced until they correspond substantially with that of the lean insulin-sensitive member, said substantial correspondence being thereafter maintained on a long-term basis.

14. A method for modifying lipid and glucose metabolism in a lean human in need of such treatment the method comprising:

administering a dopamine agonist and a prolactin stimulator to said lean human daily at different predetermined times of the day that will cause the prolactin level in the blood of said lean human to peak at substantially the same time of day as prolactin level peaks in a fat human, thereby causing the body fat content of said lean human to increase.

15. The method of claim 13 wherein the dopamine agonist is administered daily to said obese subject to increase the cellular sensitivity of the obese subject to insulin.

16. The method of claim 13 wherein the dopamine agonist is administered daily to said obese subject to reduce hyperinsulinemia.

17. The method of claim 13 wherein the dopamine agonist is administered daily to the obese subject to reduce hyperglycemia.

18. The method of claim 13 wherein the dopamine agonist is selected from the group consisting of 6-methyl-8-beta-carbobenzyloxy-aminoethyl-10 alpha-ergoline; 8-acylaminoergolenes; bromocriptine, and D-2-halo-6-alkyl-8-substituted ergolines.

19. A method for modifying and regulating at least one of lipid and glucose metabolism in a human in need of such treatment, said method comprising administering bromocriptine to said human on a timed daily basis at a first predetermined time of day in a first dosage amount sufficient to reduce hyperglycemia and hyperinsulinemia and to reduce hormonal prolactin level in the blood of said human and additionally administering metoclopramide to said human on a timed daily basis at a second predetermined time of day in a second dosage amount sufficient to increase normal prolactin level in the blood of said human; continuing said administrations for periods of time sufficient to modify and reset on a long-term basis the prolactin daily cycle of said human to mimic the low day levels and night time peak of the prolactin cycle of a lean healthy human, thereby achieving in said human at least one of the following long-term results: a reduction in insulin resistance, a reduction in fat stores, suppression of hyperinsulinemia and a reduction in hyperglycemia.

20. A method for modifying and regulating lipid and glucose metabolism in a vertebrate animal or human subject in need of such treatment comprising administering daily to said subject at a predetermined time of day a prolactin stimulator wherein said predetermined time of day is shortly before the daily peak of the prolactin level of a lean healthy member of the same species as said subject, in an amount sufficient to increase the normal prolactin level in the blood of said subject to cause said subject's daily prolactin level to peak at about the same time as the daily prolactin level of said lean healthy member of the same species.

21. The method of claim 20 wherein said subject is a human.

22. A method for treating Type II diabetes in a vertebrate animal or human subject in need of such treatment comprising administering to said subject a dopamine agonist on a daily basis at a first predetermined time of day in a first dosage amount sufficient to reduce the hormonal prolactin level in the bloodstream of said subject; and additionally administering to said subject a prolactin stimulator on a daily basis at a second predetermined time of day in a second dosage amount sufficient to increase the hormonal prolactin level in the bloodstream of said subject; and continuing said administration for periods of time sufficient to modify and reset on a long-term basis the daily prolactin cycle of said subject to mimic the low level and peak of the prolactin cycle of a lean healthy member of the same species, thereby achieving in said subject at least one of a decrease in insulin resistance, suppression of hyperinsulinemia and reduction of hyperglycemia, with or without concomitant reduction of body fat stores in said subject.

23. The method of claim 22 wherein after lapse of said periods of time, said administrations are discontinued but the modification and reset of the prolactin cycle of said subject persist thereafter on a long-term basis.

24. The method of claim 22 wherein said subject is a human and said low level is the low day level and said peak is the night time peak of the daily prolactin cycle of a lean healthy human.

* * * * *